(12) United States Patent
Di Santo

(10) Patent No.: US 12,315,137 B2
(45) Date of Patent: May 27, 2025

(54) CUTTINGS IMAGING FOR DETERMINING GEOLOGICAL PROPERTIES

(71) Applicant: Schlumberger Technology Corporation, Sugar Land, TX (US)

(72) Inventor: Simone Di Santo, Dhahran (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 244 days.

(21) Appl. No.: 18/006,017

(22) PCT Filed: Aug. 6, 2021

(86) PCT No.: PCT/US2021/044883
§ 371 (c)(1),
(2) Date: Jan. 19, 2023

(87) PCT Pub. No.: WO2022/032057
PCT Pub. Date: Feb. 10, 2022

(65) Prior Publication Data
US 2023/0351580 A1    Nov. 2, 2023

Related U.S. Application Data

(60) Provisional application No. 63/061,904, filed on Aug. 6, 2020.

(51) Int. Cl.
*G06T 7/00* (2017.01)
*E21B 21/06* (2006.01)
(Continued)

(52) U.S. Cl.
CPC ............ *G06T 7/001* (2013.01); *E21B 49/005* (2013.01); *G01N 21/27* (2013.01); *G01N 33/24* (2013.01);
(Continued)

(58) Field of Classification Search
CPC ....... E21B 49/005; G01N 33/24; G06V 10/44
See application file for complete search history.

(56) References Cited

U.S. PATENT DOCUMENTS

| 1,179,089 A | 4/1916 | Gibson |
| 7,936,374 B2 | 5/2011 | Cutler |
(Continued)

FOREIGN PATENT DOCUMENTS

| CN | 111141698 A | 5/2020 |
| EP | 3896496 A1 | 10/2021 |
| WO | 2019167030 A1 | 9/2019 |

OTHER PUBLICATIONS

Abbireddy, C.O.R. et al., "A method of estimating the form of fine particulates", Geotechnique 2009, 59(6), pp. 503-511.
(Continued)

*Primary Examiner* — Emily C Terrell
*Assistant Examiner* — Amanda H Pearson
(74) *Attorney, Agent, or Firm* — Jeffrey D. Frantz

(57) ABSTRACT

Digital image processing a digital image of sample drill cuttings retrieved from a geological formation and related methods include identifying individual zones in the image that depict at least a predetermined minimum heterogeneity of a first physical property, extracting particles in each identified zone that depict a second physical property within a predetermined quantitative range, and measuring a third physical property of each extracted particle. The first physical property may be texture, size, color, or spectral response within the zone. The second physical property may be brightness, color, contrast, hue, saturation, or wavelet energy. The third physical property may be size or color.

20 Claims, 5 Drawing Sheets

(51) Int. Cl.
| | |
|---|---|
| *E21B 49/00* | (2006.01) |
| *G01N 21/27* | (2006.01) |
| *G01N 33/24* | (2006.01) |
| *G06T 7/12* | (2017.01) |
| *G06T 7/136* | (2017.01) |
| *G06V 10/44* | (2022.01) |
| *G06V 20/10* | (2022.01) |

(52) U.S. Cl.
CPC ............... *G06T 7/12* (2017.01); *G06T 7/136* (2017.01); *G06V 10/44* (2022.01); *G06V 20/10* (2022.01); *E21B 21/066* (2013.01); *G06T 2207/30164* (2013.01)

(56) References Cited

U.S. PATENT DOCUMENTS

| | | | |
|---|---|---|---|
| 8,170,799 | B2 | 5/2012 | Dvorkin et al. |
| 9,142,045 | B1* | 9/2015 | Cavanaugh ........... G06T 11/206 |
| 9,412,023 | B1 | 8/2016 | Hurley |
| 9,507,047 | B1 | 11/2016 | Dvorkin |
| 9,652,684 | B2 | 5/2017 | Keskes et al. |
| 10,927,671 | B1 | 2/2021 | Tonner et al. |
| 11,188,794 | B2 | 11/2021 | Yao et al. |
| 2005/0276513 | A1 | 12/2005 | Ojanen |
| 2010/0128932 | A1 | 5/2010 | Dvorkin |
| 2012/0123756 | A1 | 5/2012 | Wang |
| 2013/0073207 | A1 | 3/2013 | Ganz |
| 2013/0120763 | A1 | 5/2013 | Grenet |
| 2013/0259190 | A1 | 10/2013 | Walls |
| 2013/0308831 | A1* | 11/2013 | Dvorkin ................ G06T 7/0004 382/109 |
| 2014/0046628 | A1 | 2/2014 | Ligneul |
| 2015/0043787 | A1 | 2/2015 | Fredrich |
| 2016/0370274 | A1 | 12/2016 | Rowe et al. |
| 2017/0085860 | A1 | 3/2017 | Zhang |
| 2018/0101962 | A1 | 4/2018 | Takizawa |
| 2018/0180524 | A1 | 6/2018 | Francois |
| 2019/0212272 | A1 | 7/2019 | Scoullar |
| 2019/0338637 | A1* | 11/2019 | Francois ................ E21B 49/08 |
| 2019/0368336 | A1* | 12/2019 | Hammond .............. E21B 47/11 |
| 2020/0025667 | A1 | 1/2020 | Allo |
| 2020/0143205 | A1 | 5/2020 | Yao |
| 2020/0150307 | A1 | 5/2020 | Myers |
| 2020/0157929 | A1 | 5/2020 | Torrione |
| 2021/0041588 | A1 | 2/2021 | Chen |
| 2021/0254457 | A1 | 8/2021 | Anifowose |
| 2021/0312674 | A1 | 10/2021 | Abrol et al. |
| 2023/0184992 | A1 | 6/2023 | AlBahrani |
| 2023/0220761 | A1 | 7/2023 | Yamada et al. |
| 2023/0220770 | A1 | 7/2023 | Yamada et al. |
| 2023/0351580 | A1 | 11/2023 | Di Santo |
| 2024/0054766 | A1 | 2/2024 | Yu |

OTHER PUBLICATIONS

Barrett, P. J. "The shape of rock particles, a critical review", Sedimentology, 1980, 27, pp. 291-303.
Caicedo, J. C. et al., "Nucleus segmentation across imaging experiments: the 2018 Data Science Bowl", Nature Methods, 2019, 16, pp. 1247-1253.
Dunlop, H. et al., "Multi-scale Features for Detection and Segmentation of Rocks in Mars Images", 2007, 10.1109/CVPR.2007.383257, 7 pages.
Feng, L. et al., "Robust Nucleus Detection with Partially Labeled Exemplars", IEEE Access (7), 2019, pp. 162169-162178.
Gaetano, R. et al., "Hierarchical Texture-Based Segmentation of Multiresolution Remote-Sensing Images", IEEE Transactions on Geoscience and Remote Sensing, 2009, 47(7), pp. 2129-2141.
He, K. et al., "Mask R-CNN", Computer Vision (ICCV), IEEE International Conference on Computer Vision, 2017, pp. 2980-2988.
He, K. et al., "Deep Residual Learning for Image Recognition", 2016 IEEE International Conference on Computer Vision, 2016, pp. 770-778.
Huo, F. et al., "Novel lithology identification method for drilling cuttings under PDC bit condition", Journal of Petroleum Science and Engineering, 2021, 205, 15 pages.
Jung, H. et al., "An automatic nuclei segmentation method based on deep convolutional neural networks for histopathology images", BMC Biomedical Engineering, 2019, 1:24, 12 pages.
Lin, T. Y., et al., "Microsoft COCO: Common Objects in Context", ECCV 2014: Computer Vision—ECCV 2014, pp. 740-755.
Lin, T.-Y., et al., "Feature Pyramid Networks for Object Detection", Computer Vision and Pattern Recognition (CVPR), IEEE International Conference on Computer Vision 2017, pp. 936-944.
Rahmani, H. et al., "Automated segmentation of gravel particles from depth images of gravel-soil mixtures", Compute and Geosciences, 2019, 128, pp. 1-10.
Ravali, K. et al., "Graph-Based High Resolution Satellite Image Segmentation for Object Recognition", The International Archives of the Photogrammetry, Remote Sensing and Spatial Information Sciences, 2014, vol. XL-8. pp. 913-917.
SANXO—Scope HD U4 Express: Industrial Microscope downloaded from the internt at [https://sanxo.eu/sanxo-scope-hd-u4-express-industrial-microscope/] on Apr. 21, 2022, 8 pages.
Shi, J. et al., "Normalized Cuts and Image Segmentation", IEEE Transactions on Pattern Analysis and Machine Intelligence, 2000, 22(8), pp. 888-905.
Thurley, M. J., "Automated Image Segmentation and Analysis of Rock Piles in an Open-Pit Mine", International Conference on Digital Image Computing: Techniques and Applications (DICTA), 2013, 10.1109/DICTA.2013.6691484, 8 Pages.
Ting, G. et al., "Rock Particle Image Segmentation Based on Improved Normalized Cut", International Journal of Control and Automation, 2017, 10(4), pp. 271-286.
Wang, W., "Rock Particle Image Segmentation and Systems", in Pattern Recognition Techniques, Technology and Applications, Book edited by: Peng-Yeng Yin, Nov. 2008, I-Tech, Vienna, Austria, 10.5772/6242, 30 pages.
Wikipedia "Semi Supervised Learning" downloaded from the internet at [https://en.wikipedia.org/wiki/Semi-supervised_learning] retrieved on Apr. 21, 2022, 7 pages.
Wikipedia "Transfer Learning" downloaded from the internet at [https://en.wikipedia.org/wiki/Transfer_learning] retrieved on Apr. 21, 2022, 5 pages.
Wikipedia "Run-length encoding", downloaded from the internet at [https://en.wikipedia.org/wiki/Run-length_encoding] retrieved on Apr. 21, 2022, 3 pages.
"pytorch/vision" downloaded from the internet at [https://github.com/pytorch/vision] retrieved on Apr. 21, 2022, 6 pages.
"Mongoose Pro Dynamic dual-motion shaker", retrieved from the internet: [https://www.slb.com/drilling/drilling-fluids-and-well-cementing/solids-control/shale-shakers/mongoose-pro-shale-shaker] Apr. 19, 2022, 9 pages.
Search Report and Written Opinion of International Patent Application No. PCT/US2021/044883 dated Nov. 16, 2021, 10 pages.
Using colorcheck. Imatest, Retrieved Mar. 4, 2022, from https://www.imatest.com/docs/colorcheck/, 26 pages.
Sharpness: What is it and how it is measured. Imatest, Retrieved Mar. 4, 2022, from https://www.imatest.com/docs/sharpness/, 17 pages.
Beard et al., Influence of texture on porosity and permeability of unconsolidated sand. American Association of Petroleum Geologists Bulletin, vol. 27, No. 2, Feb. 1973, p. 349-369.
Ameen et al., The function of fractures and in-situ stresses in the Khuff reservoir performance, onshore fields, Saudi Arabia, American Association of Petroleum Geologists Bulletin, vol. 94, No. 1, Jan. 2010, pp. 27-60.
Blaschke et al., Object-Based Image Analysis. Springer. p. 37. ISBN: 978-3-540-77057-2, 2008, 30 pages.
International Search Report and Written Opinion issued in PCT Application No. PCT/US2023/015998 dated Jul. 11, 2023, 11 pages.
International Search Report and Written Opinion issued in PCT Application No. PCT/US2023/070658 dated Nov. 8, 2023, 12 pages.

(56) References Cited

OTHER PUBLICATIONS

Office Action issued in U.S. Appl. No. 17/647,407 dated Jun. 25, 2024, 22 pages.
International Preliminary Report on Patentability issued in International Patent application PCT/US2023/060240, dated Jun. 20, 2023, 6 pages.
International Preliminary Report on Patentability issued in International Patent application PCT/US2022/053454, dated Jun. 20, 2024, 6 pages.
Office Action issued in U.S. Appl. No. 17/647,412 dated Jul. 18, 2024, 10 pages.
International Preliminary Report on Patentability issued in the PCT Application No. PCT/US2021/044883 mailed Feb. 16, 2023, 7 pages.
International Search Report and Written Opinion issued in PCT Application No. PCT/US2022/053454 dated Apr. 25, 2023, 10 pages.
International Search Report and Written Opinion issued in PCT Application No. PCT/US2022/060240 dated Apr. 28, 2023, 10 pages.
Liang, Z. et al., "A particle shape extraction and evaluation method using a deep convolutional neural network and digital image processing", Powder Technology, 2019, 353, pp. 156-170.
Becerra, D. et al., "Generating a labeled data set to train machine learinig algorithms for lithologic classification of drill cuttings", Special section: Machine learning for image-based geologic interpretation, SEG, 2022, pp. SE85-SE100.

* cited by examiner

CUTTINGS IMAGING FOR DETERMINING GEOLOGICAL PROPERTIES

CROSS-REFERENCE TO RELATED APPLICATIONS

This application is a National Stage Entry of International Application No. PCT/US2021/044883, filed Aug. 6, 2021, which claims priority to and the benefit of U.S. Provisional Application No. 63/061,904, titled "Method for analyzing a drill cuttings sample," filed Aug. 6, 2020, the entirety of which is incorporated herein by reference.

BACKGROUND

Surface logging is a wellsite service providing early indications about drilled rocks and reservoir potential. For example, a wellsite operator, known as a "mud logger," may attempt to perform lithology identification from drill cuttings returning from a well in order to reconstruct a geology map of the well. The mud logger creates a manual description based on images and acid tests. For each sample, the mud logger may examine cutting samples (e.g., through binoculars or other magnifying means) and attempt to recognize different rock types in the samples. If the rock types are not visually clear, some of the cuttings may be isolated for acid tests and final identification. The mud logger then attempts to quantify proportions of the different rock types from the samples. Using this information, a reconstruction of the well formation can be performed to create a lithology column. However, manual rock type identification and quantification can be subjective (e.g., biased by the mud logger's geological background) and time-consuming.

SUMMARY

This summary is provided to introduce a selection of concepts that are further described below in the detailed description. This summary is not intended to identify indispensable features of the claimed subject matter, nor is it intended for use as an aid in limiting the scope of the claimed subject matter.

Embodiments of the present disclosure relate to a method that includes processing a digital image of sample drill cuttings retrieved from a geological formation. The digital image processing includes identifying individual zones in the image that depict at least a predetermined minimum heterogeneity of a first physical property. In each identified zone, particles that depict a second physical property within a predetermined quantitative range are extracted. A third physical property of each extracted particle is then measured. The first physical property may be texture, size, color, or spectral response within the zone. The second physical property may be brightness, color, contrast, hue, saturation, or wavelet energy. The third physical property may be size or color.

Embodiments of the present disclosure also relate to an apparatus including a processing system having a processor and a memory storing an executable computer program code that, when executed by the processor, processes a digital image of sample drill cuttings retrieved from a geological formation. The digital image processing includes identifying individual zones in the image that depict at least a predetermined minimum heterogeneity of a first physical property, extracting particles in each identified zone that depict a second physical property within a predetermined quantitative range, and measuring a third physical property of each extracted particle.

These and additional aspects of the present disclosure are set forth in the description that follows, and/or may be learned by a person having ordinary skill in the art by reading the material herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
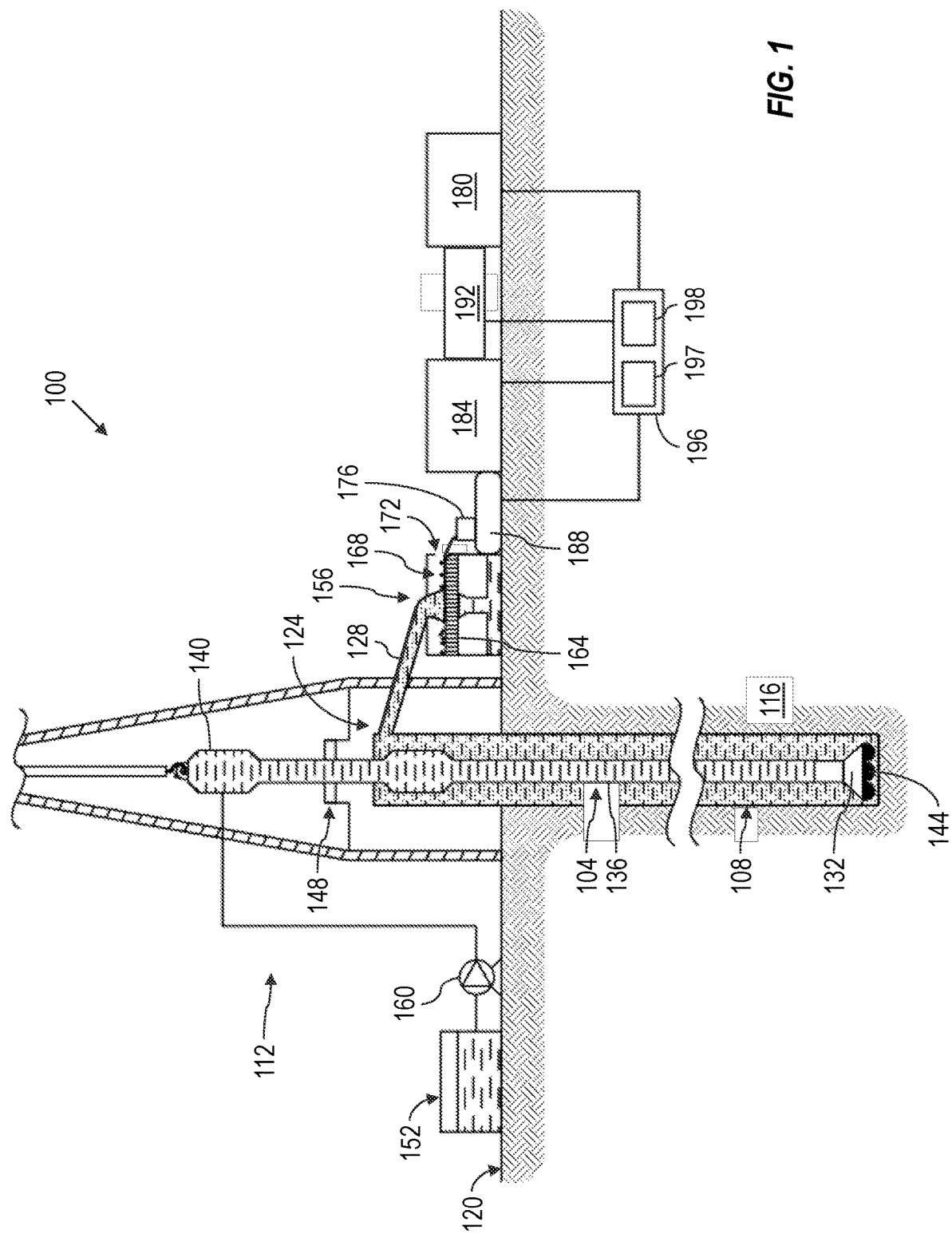
FIG. 1 is a schematic view of at least a portion of an example implementation of a wellsite installation according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity and does not in itself dictate a relationship between the various embodiments and/or configurations discussed.

FIG. 1 is a schematic view of at least a portion of an example implementation of an installation 100 for drilling a wellbore for an oil/gas well at a wellsite according to one or more aspects of the present disclosure. The installation 100 includes a rotary drilling tool 104, for drilling a wellbore (cavity) 108, as well as a surface installation 112 where drilling pipes are placed in the wellbore 108. The wellbore 108 is formed in a geologic formation (substratum) 116 by the rotary drilling tool 104. At the wellsite surface 120, a well head 124 having a discharge pipe 128 closes the wellbore 108.

The drilling tool 104 includes a drilling head 132, a drill string 136, and a liquid injection head 140. The drilling head 132 includes a drill bit 144 for drilling through the rocks of the geologic formation 116. The drill string 136 is formed by a set of hollow drilling pipes through which drilling fluid is pumped from the surface 120 to the drilling head 132 via the liquid injection head 140. The drilling fluid is a drilling mud, such as a water-based or oil-based drilling mud.

The surface installation 112 includes a support (e.g., a top drive) 148 for supporting the drilling tool 104 and driving it in rotation, an injector 152 for injecting the drilling fluid, and a shale shaker 156. The injector 152 is hydraulically connected to the injection head 140 in order to introduce and pump (e.g., via one or more pumps 160) the drilling fluid into the drill string 136. The shale shaker 156 collects the drilling fluid, charged with drill cuttings, flowing out from the discharge pipe 128. The shale shaker 156 includes a sieve 164 allowing the separation of the solid drill cuttings 168 from the drilling mud. The shale shaker 156 also includes an outlet 172 for evacuating the drill cuttings 168.

One or more aspects of the present disclosure relate to methods and systems for analyzing the cuttings 168. Such systems may be situated at the wellsite, such as in the vicinity of the shale shaker 156, as depicted in FIG. 1, or in a cabin or other facility a few hectometers from the shale shaker 156. Such systems may instead be situated away from the wellsite, such as in a laboratory.

The example of such systems depicted in FIG. 1 includes a container or other sampler 176 for collecting the cuttings 168 discharged from the outlet 172. An imaging device 180 for taking one or more multi-pixel digital images of a sample of the cuttings 168. The imaging device 180 (and other components) is used to identify or otherwise predict one or more properties of the geologic formation 116 via automatic analysis of the image generated by the imaging device 180. The imaging device 180 may be or may include an optical or electronic microscope or a camera.

The system may also include a preparation unit 184, such as may wash, dry, separate, and/or otherwise prepare the sampled cuttings 168 prior to imaging. However, the preparation unit 184 is optional, or perhaps able to be bypassed, such that cuttings 168 may be imaged just after having been sampled. It is to be noted that the cuttings 168 may not be separated from each other before being imaged by the imaging device 180.

The drill cuttings may be automatically sampled, including being transferred to the preparation device 184 (when utilized) and then to imaging device 180 via a conveyor 188 and a transport device 192. The preparation and/or imaging may be performed automatically via various devices commanded via a sequence of actions of the preparation device 184 and the imaging device 180, among others. However, other conveyance devices may also or instead be used for transporting the cuttings 168.

The system also includes a processing system 196 connected to at least the imaging device 180 in order to receive images taken by the imaging device 180. The processing system 196 may be or may include at least a portion of one or more instances of the processing system 200 described below with respect to FIG. 2. The processing system 196 may include an analysis module 197 operable to analyze the image taken by the imaging device 180, as described below. The processing system 196 may also, such as in implementations in which the sampling and/or conveyance and/or preparation and/or imaging are automatic, include a control unit 198 for controlling the preparation and imaging of the sample. In such implementations, among others within the scope of the present disclosure, the processing system 196 may also able to communicate with the conveyor 188, the preparation device 185, the transport device 192, and the imaging device 180. The processing system 196 may also communicate with other modules at the wellsite, such as to determine the depth from which sample drill cuttings are retrieved, perhaps via known or future-developed processes (e.g., based on lag time). The processing system 196 may be situated in the vicinity of the imaging device 180, or remotely from the imaging device 180. The processing system 196 may also include several modules situated at different locations, such as one situated in the vicinity of the imaging device 180 and one situated remotely from the imaging device 180. Each such module may be or may include at least a portion of the processing system 200 described below with respect to FIG. 2.

It is to be noted that the system depicted in FIG. 1 is an example implementation. It has been described when the sample of cuttings is automatically handled. However, in other implementations within the scope of the present disclosure, the sample may be manually collected and transferred by an operator to a cabin or to a lab, at which the sample may be imaged and optionally prepared. Implementations of systems within the scope of the present disclosure may also include just the imaging device 180 and the processing system 196. Such systems may be utilized to, for example, analyze drill cuttings and/or other types of rock samples.

Figure 2:
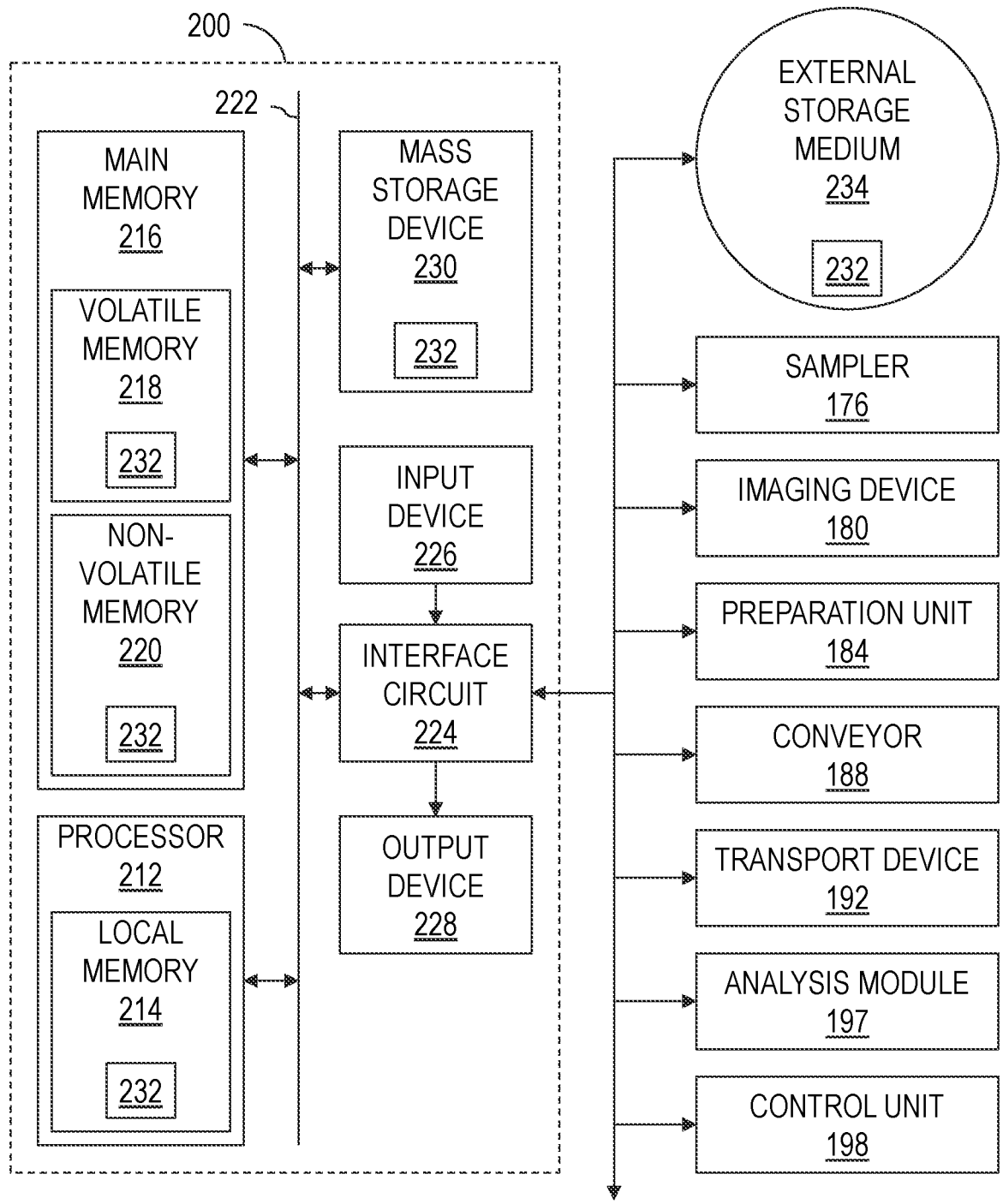
FIG. 2 is a schematic view of at least a portion of an example implementation of a processing system according to one or more aspects of the present disclosure.

FIG. 2 is a schematic view of at least a portion of an example implementation of a processing system 200 according to one or more aspects of the present disclosure. The processing system 200 may be or form at least a portion of one or more equipment controllers, processors, processing systems, and/or other electronic devices shown in (or otherwise associated with) FIG. 1, including for performing at least a portion of the method described herein. For example, the processing system 200 (or instances, portions, or instances of portions thereof) may be, form, or otherwise operate in conjunction with at least a portion of the sampler 176, the imaging device 180, the preparation unit 184, the conveyor 188, the transport device 192, the processing system 196, the analysis module 197, and/or the control unit 198.

The processing system 200 may be or may include, for example, one or more processors, controllers, special-purpose computing devices, personal computers (PCs, e.g., desktop, laptop, and/or tablet computers), personal digital assistants, smartphones, industrial PCs (IPCs), programmable logic controllers (PLCs), servers, internet appliances, and/or other types of computing devices. Although it is possible that the entirety of one or more instances of the processing system 200 is implemented within one device, it is also contemplated that one or more components or functions of the processing system 200 may be implemented across multiple devices, some or an entirety of which may be at the wellsite and/or remote from the wellsite.

The processing system 200 may include a processor 212, such as a general-purpose programmable processor. The processor 212 may include a local memory 214 and may execute computer/machine-readable and executable program code instructions 232 (i.e., computer program code) present in the local memory 214 and/or another memory device. The processor 212 may be, may include, or be implemented by one or more processors of various types suitable to the local application environment, and may include one or more of general-purpose computers, special-purpose computers, microprocessors, digital signal processors (DSPs), field-programmable gate arrays (FPGAs), application-specific integrated circuits (ASICs), and processors based on a multi-core processor architecture, as non-limiting examples. Examples of the processor 212 include one or more INTEL microprocessors, microcontrollers from the ARM and/or PICO families of microcontrollers, and embedded soft/hard processors in one or more FPGAs.

The processor 212 may execute, among other things, the program code instructions 232 and/or other instructions and/or programs to implement the example methods and/or operations described herein. For example, the program code instructions 232, when executed by the processor 212 of the processing system 200, may cause the processor 212 to receive and process sensor data, such as unknown rock sample images obtained by the imaging device 180. The program code instructions 232, when executed by the processor 212 of the processing system 200, may also or instead cause the processor 212 to output control data (i.e., control commands) to cause the control of one or more portions or pieces of wellsite equipment, such as the sampler 176, the imaging device 180, the preparation unit 184, the conveyor 188, the transport device 192, the analysis module 197, and/or the control unit 198, perhaps including to perform one or more aspects of the example methods and/or operations described herein.

The processor 212 may be in communication with a main memory 216, such as may include a volatile memory 218 and a non-volatile memory 220, perhaps via a bus 222 and/or other communication means. The volatile memory 218 may be, may include, or be implemented by various types of random-access memory (RAM), such as static RAM (SRAM), dynamic RAM (DRAM), fast page mode dynamic random-access memory (FPM DRAM), extended data out DRAM (EDO DRAM), synchronous DRAM (SDRAM), double data rate SDRAM (DDR SDRAM (including DDR2, DDR3, DDR4, DDR5, etc.)), RAMBUS DRAM (RDRAM), and/or other types of RAM devices. The non-volatile memory 220 may be, may include, or be implemented by read-only memory, flash memory, and/or other types of memory devices. One or more memory controllers (not shown) may control access to the volatile memory 218 and/or non-volatile memory 220.

The processing system 200 may also include an interface circuit 224, which is in communication with the processor 212, such as via the bus 222. The interface circuit 224 may be, may include, or be implemented by various types of standard interfaces, such as an Ethernet interface, a universal serial bus (USB), a third-generation input/output (3GIO) interface, a wireless interface, a cellular interface, and/or a satellite interface, among others. The interface circuit 224 may include a graphics driver card. The interface circuit 224 may include a communication device, such as a modem or network interface card to facilitate exchange of data with external computing devices via a wide area network (WAN, e.g., an Ethernet connection, a DSL, a telephone line, a coaxial cable, a cellular telephone system, a satellite communication system, etc.).

The processing system 200 may be in communication with various sensors, video cameras, actuators, processing devices, equipment controllers, and other devices of the well construction system via the interface circuit 224, perhaps including the sampler 176, the imaging device 180, the preparation unit 184, the conveyor 188, the transport device 192, the processing system 196, the analysis module 197, and/or the control unit 198. The interface circuit 224 can facilitate communications between the processing system 200 and one or more devices by utilizing one or more communication protocols, such as an Ethernet-based network protocol (e.g., ProfiNET, OPC, OPC/UA, Modbus TCP/IP, EtherCAT, UDP multicast, Siemens S7 communication, etc.), a proprietary communication protocol, and/or another communication protocol.

One or more input devices 226 may also be connected to the interface circuit 224. The input devices 226 may permit a human user to enter the program code instructions 232, which may be or may include control data, operational parameters, operational set-points, a well construction plan, and/or a database of operational sequences. The program code instructions 232 may further include modeling or predictive routines, equations, algorithms, processes, applications, and/or other programs operable to perform example methods and/or operations described herein. The input devices 226 may be, may include, or be implemented by a keyboard, a mouse, a joystick, a touchscreen, a trackpad, a trackball, an isopoint, and/or a voice recognition system, among other examples. One or more output devices 228 may also be connected to the interface circuit 224. The output devices 228 may permit for visualization or other sensory perception of various data, such as sensor data, status data, and/or other example data. The output devices 228 may be, may include, or be implemented by video output devices (e.g., a liquid crystal display (LCD), a light-emitting diode (LED) display, a cathode ray tube (CRT) display, a touchscreen, etc.), printers, and/or speakers, among other examples.

The processing system 200 may include a mass storage device 230 for storing data and program code instructions 232. The mass storage device 230 may be connected to the processor 212, such as via the bus 222. The mass storage device 230 may be or may include a tangible, non-transitory, computer-readable storage medium, such as a hard disk drive, a compact disk (CD) drive, and/or digital versatile disk (DVD) drive, among other examples.

The processing system 200 may be communicatively connected with an external storage medium 234 via the interface circuit 224. The external storage medium 234 may be or may include a removable storage medium (e.g., CD or DVD), such as may be operable to store data and program code instructions 232.

As described above, the program code instructions 232 may be stored in the mass storage device 230, the main memory 216, the local memory 214, and/or the removable storage medium 234. Thus, the processing system 200 may be implemented in accordance with hardware (perhaps implemented in one or more chips including an integrated circuit, such as an ASIC), or may be implemented as software or firmware for execution by the processor 212. In the case of firmware or software, the implementation may be provided as a computer program product including a non-transitory, computer-readable medium or storage structure storing computer program code instructions 232 (i.e., software or firmware) for execution by the processor 212. The program code instructions 232 may include program instructions or computer program code that, when executed by the processor 212, may perform and/or cause performance of one or more aspects of the methods, processes, and/or operations described herein.

Figure 3:
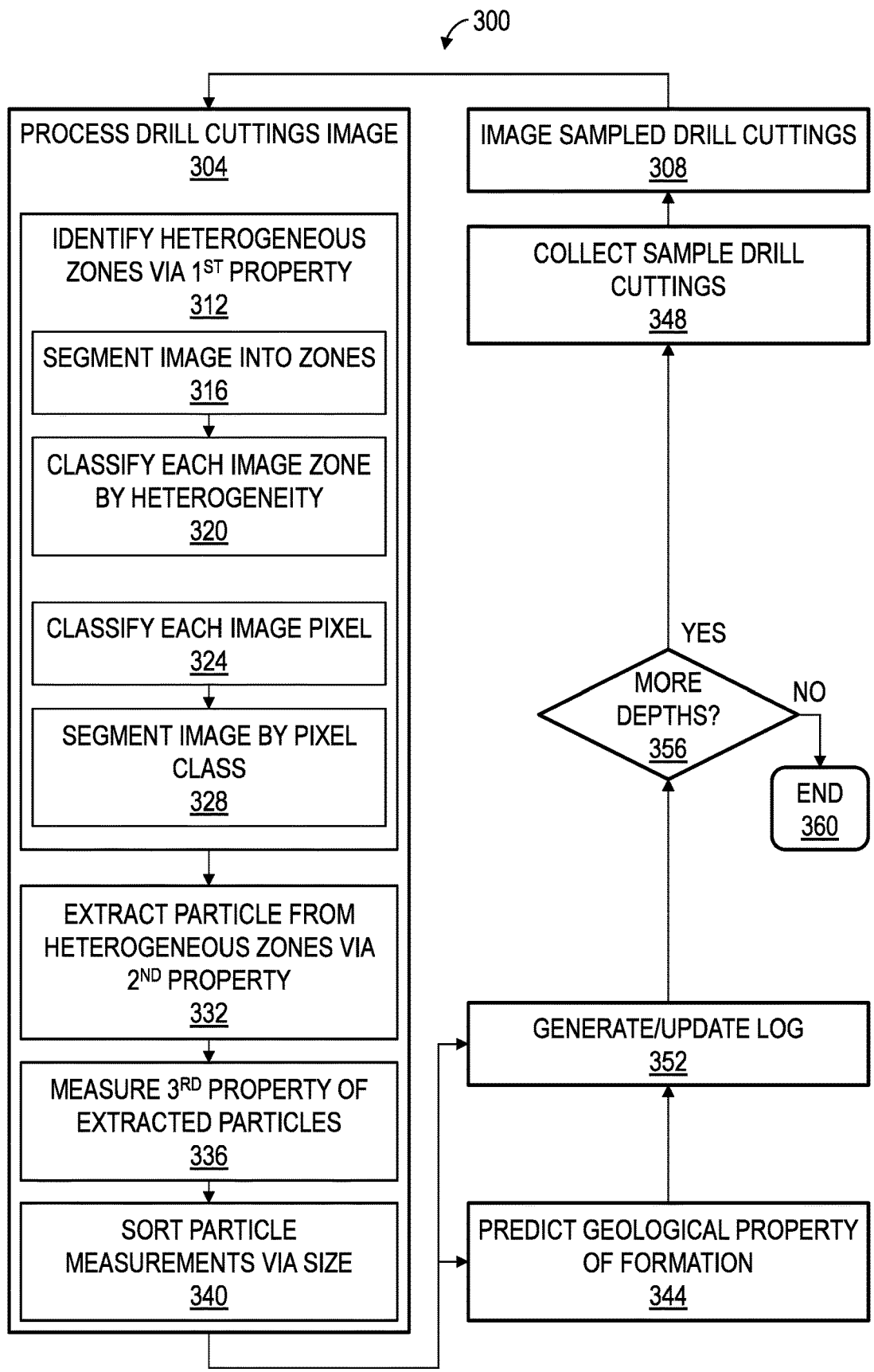
FIG. 3 is a flow-chart diagram of at least a portion of an example implementation of a method according to one or more aspects of the present disclosure.
Figure 4:
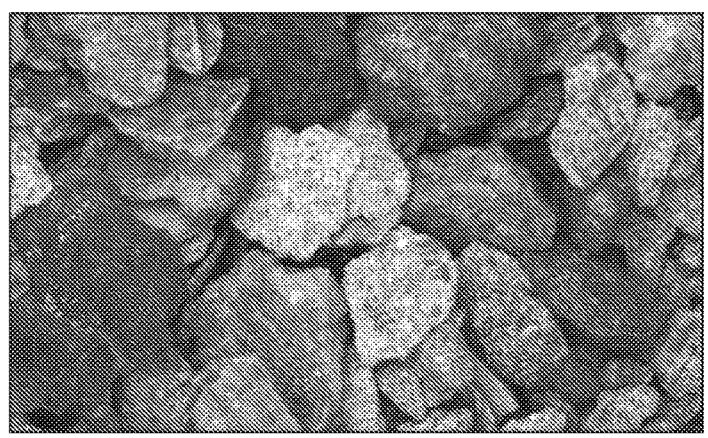
FIGS. 4-7 depict example results of various stages of digital image processing according to one or more aspects of the method shown in FIG. 3.

FIG. 3 is a flow-chart diagram of at least a portion of an implementation of a method 300 according to one or more aspects of the present disclosure. The method 300 may be utilized in conjunction with the apparatus depicted in FIGS. 1 and/or 2 (and/or other apparatus also within the scope of the present disclosure). For example, the method 300 may be utilized to determine one or more properties of a sample plurality of the drill cuttings 168 by processing 304 a multi-pixel digital image of the sample. An example of such digital image is shown in FIG. 4. The example digital image depicted in FIG. 4 is shown in grayscale, although other implementations also within the scope of the present disclosure may utilize digital images that are multicolored, black and white, and/or other formats. The method may include imaging 308 the sample drill cuttings 168 by an imager, such as the imaging device 180 and/or others. The image processing 304 may be performed by a processing system, such as the processing system 196 and/or other processing systems perhaps having one or more characteristics and/or functions as described above with respect to one or more components of the processing system 200 shown in FIG. 2.

The image processing 304 includes identifying 312 individual zones in the image that depict at least a predetermined minimum heterogeneity of a first physical property. The first physical property may be texture, size, color, or spectral response within the zone, such that the predetermined minimum heterogeneity may be texture, size, color, or spectral response values that vary by at least 50% (for example) within an individual zone. For example, identifying 312 the heterogeneous zones may include segmenting 316 the image (e.g., based on detected boundaries between each drill cutting, i.e., one zone per individual drill cutting recognized in the image) and classifying 320 each zone based on the heterogeneity depicted therein, such that the identified 312 zones are those segments that individually depict at least the predetermined minimum heterogeneity of the first physical property.

However, other methods for segmenting and classifying the image to identify 312 the heterogeneous zones are also within the scope of the present disclosure. According to some embodiments, a method for identifying 312 the heterogeneous zones may include classifying 324 each pixel of the image based on the depicted first physical property of that pixel being within one of a plurality of predetermined value ranges of the first physical property, and then segmenting 328 the image based on the pixel classifications, such that the identified 312 zones are those segments that individually depict at least the predetermined minimum heterogeneity of the first physical property. For example, when the first physical property is texture or grain size, the predetermined value ranges may be size intervals of five microns ($\mu m$) between predetermined minimum and maximum values (e.g., 10 $\mu m$ to 200 $\mu m$). Similarly, when the first physical property is color, the predetermined value ranges may be wavelength intervals of 10 nanometers (nm) between 400 nm (i.e., blue) and 700 nm (i.e., red), or when the first physical property is spectral response, the predetermined value ranges may be wavelength intervals of 20 nm between 300 nm and 1000 nm. However, other value ranges and intervals are also within the scope of the present disclosure. In such implementations, the image segmenting 328 may be based on neighboring ones or clusters of the pixels being classified in the same one of the predetermined value ranges.

In each of the example implementations of identifying 312 the heterogeneous zones, among other methods within the scope of the present disclosure, the individual identified 312 zones may be those that depict at least the predetermined minimum heterogeneity of the first physical property and at least one other predetermined minimum heterogeneity of at least one other physical property. For example, the first physical property and the at least one other physical property may collectively include at least two of texture, size, color, and spectral response within the zone.

Regardless of the method utilized to segment and classify zones of the obtained 308 image, the zones may be classified as either "grainy" (e.g., at least minimum heterogeneities of different textures, different sizes, and/or different spectral/color responses), "laminar" (heterogeneity with a linear and elongated shape where contrast variability is perpendicular to the longest axes), "homogenous" (heterogeneities below a predetermined minimum or not distinguishable and/or measurable), or "mixed" (combination of at least a minimum of two or each of grainy, laminar, and homogenous). In some embodiments, the zones may be classified as either grainy or non-grainy.

The image processing 304 also includes, in each identified 312 zone, extracting 332 particles that depict a second physical property within a predetermined quantitative range. For example, the second physical property may be brightness, color, contrast, hue, saturation, wavelet energy, and/or others. In this context, it is noted that hue is representative of the color itself, saturation is the expression of the color intensity and/or purity, and brightness represents the brilliance. The wavelet energy may be obtained by applying a wavelet transform to the identified 312 zone, or via a Haralick indicator.

Figure 8:
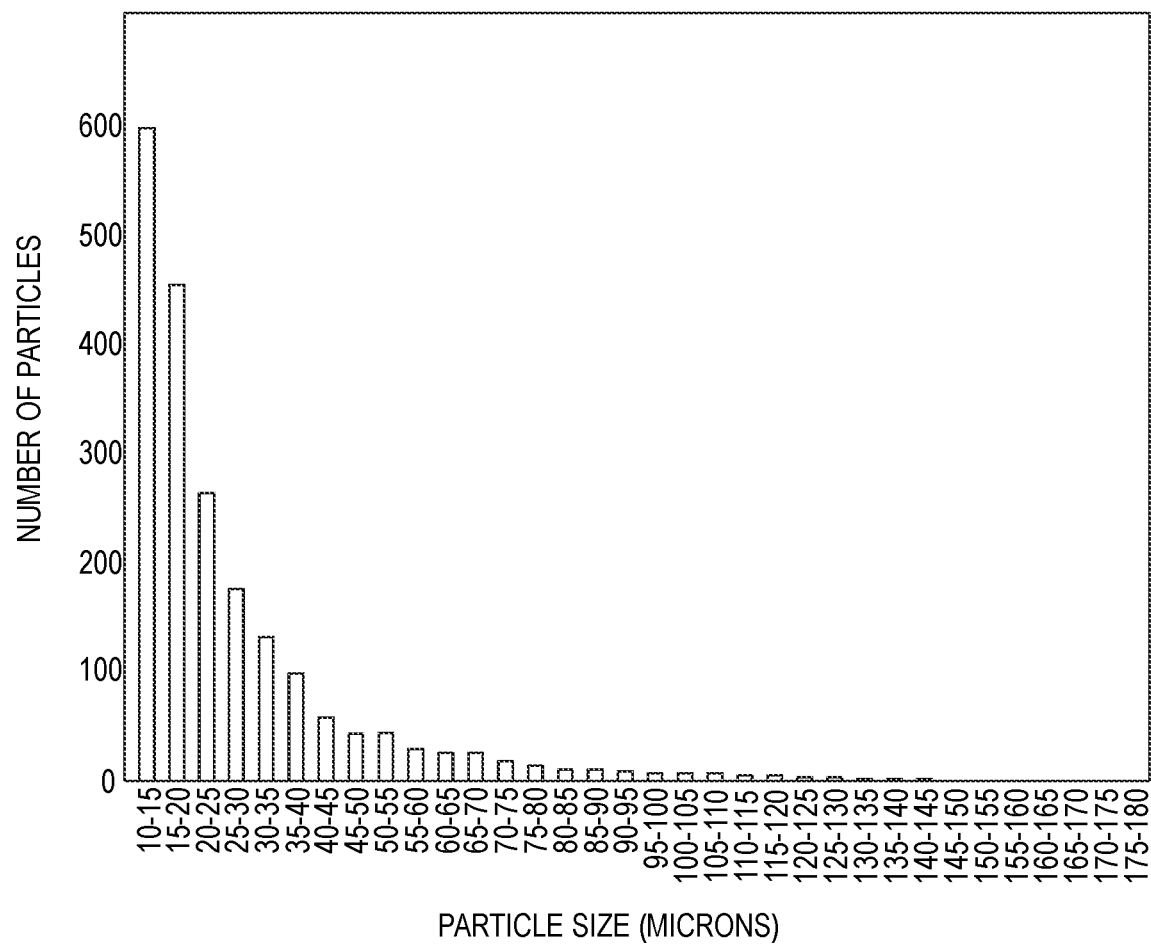
FIG. 8 is a graph depicting example results of the method shown in FIG. 3.

The image processing 304 also includes measuring 336 a third physical property of each extracted 332 particle. The third physical property may be size, color, and/or others. The image processing 304 may also include sorting 340 the third physical property measurements 336 into a plurality of predetermined value ranges. For example, the predetermined value ranges may be size intervals of 5 $\mu m$ between 10 $\mu m$ and 200 $\mu m$, color wavelength intervals of 10 nm between 400 nm and 700 nm, or spectral response wavelength intervals of 20 nm between 300 nm and 1000 nm. However, other value ranges and intervals are also within the scope of the present disclosure. An example result of the sorting 340 is depicted by the graph shown in FIG. 8.

The third physical property may be measured 336 utilizing the number of pixels in the image associated to each grain of the extracted 332 particles, as well as the resolution of the image. For example, one pixel may be equivalent to about 10 $\mu m$, such that a grain spanning three pixels can be measured as having a size of 30 $\mu m$. However, due to the Nyquist sampling rule, the grain size measurable lower limit may be forced to a grain size of at least 2×2 pixels, meaning that, depending on the camera resolution, smaller grain sizes may have to be estimated via statistical and/or machine learning methods. In the example shown in FIGS. 4-7 described below, the lower measurement limit given by the actual picture resolution can be estimated as 20 $\mu m$, but with higher resolution cameras the limit could be as small as 1 $\mu m$.

The method 300 may further include predicting 344 at least one geological property of the geological formation utilizing the sorted 340 third physical property measurements. Predicting 344 the at least one geological property may include predicting which one or more of a predetermined plurality of rock types are present in the geological formation 116. For example, the predetermined rock types may include igneous, sedimentary, and metamorphic rocks, or specific examples of each (e.g., granite, sandstone, limestone, slate, and marble). Predicting 344 the at least one geological property may further include predicting a quantity of each of the one or more rock types predicted to be present in the geological formation 116. The at least one predicted 344 geological property may also or instead include one or more of grain size, color, and porosity of the geological formation 116.

The method 300 may also include collecting 348 the sample plurality of drill cuttings after retrieval from a wellbore 108 while drilling into the geological formation 116 to form the wellbore 108, prior to imaging 308 the collected 348 sample plurality of drill cuttings to obtain the digital image. Such implementations of the method 300 may be utilized when the above-described cuttings analysis equipment is situated at the wellsite, in contrast to other implementations of the method 300 (also within the scope of the present disclosure) utilized when the cuttings analysis equipment is situated away from the wellsite, such as in a laboratory.

The sorted 340 particle measurements, and perhaps the predicted 344 geologic property(ies) of the formation 116, may also be utilized to generate and/or update 352 a time-based and/or depth-based log. For example, it may be determined 356 that additional (e.g., newly formed) depths of the wellbore 108 are also to be investigated via the above-described image processing 304, in which case the image processing 304 may be repeated on each of a plurality of additional digital images of a corresponding one of a plurality of additional samples of drill cuttings retrieved 348 from the geological formation 116 at corresponding subsequent times during the drilling operation. Otherwise, the method 300 may end 360.

Figure 5:
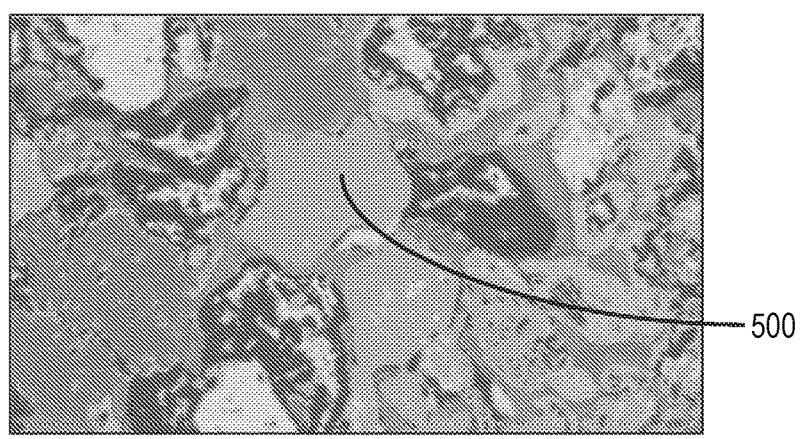

FIG. 4 is an example digital image resulting from imaging 308 a sample plurality of drill cuttings. FIG. 5 depicts an example output of the segmenting processes 316/328 in which different shades of gray correspond to the category in which each portion (e.g., each pixel or group of pixels) of the image has been classified. However, other color schemes may also be utilized. The four categories used in the example depicted in FIG. 5 are grainy, laminar, homogeneous, and mixed, as described above, although other implementations within the scope of the present disclosure may utilize otherwise defined categories, such as just two categories (e.g., grainy and non-grainy). In the example of FIG. 5, the grainy category is depicted by the shade of gray denoted by reference number 500.

Figure 6:
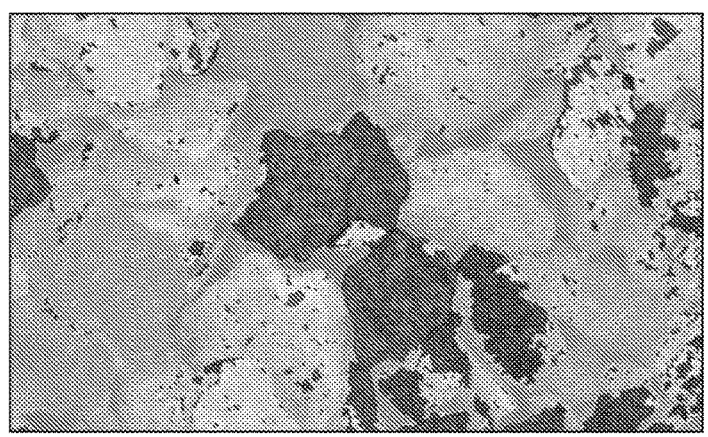

FIG. 6 depicts an example result of the heterogeneous zone identification 312, where the identified 312 zones that depict at least the predetermined minimum heterogeneity of the first physical property have been extracted and the remaining portions of the image are masked. FIG. 6 also depicts that the identified 312 zones may be refined with appropriate algorithms, such as erosion (to remove) and hole-filling algorithms (possibly with previous thresholding to obtain a black and white image), in order to obtain a better definition of the identified 312 zones.

Figure 7:
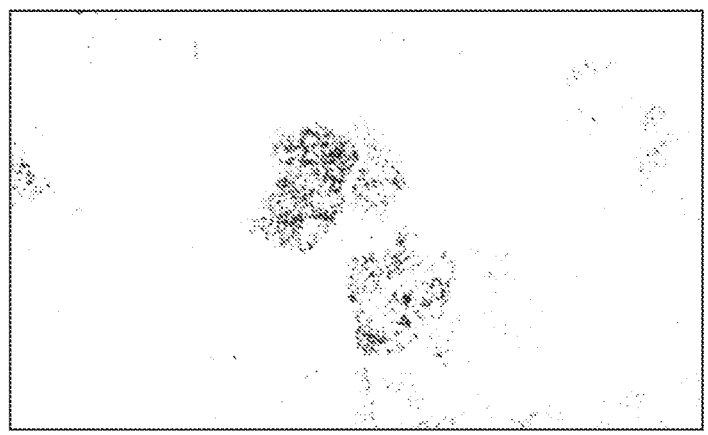

FIG. 7 depicts an example result from the particle extraction 232. In the example of FIG. 7, the bright particles have been extracted, but the extraction method can be applied to other kinds of grain color or contrast with relevant geological inferred information.

In view of the entirety of the present disclosure, a person having ordinary skill in the art will readily recognize that the present disclosure introduces a method including processing a digital image of a sample plurality of drill cuttings retrieved from a geological formation, where the digital image processing includes: identifying individual zones in the image that depict at least a predetermined minimum heterogeneity of a first physical property; in each identified zone, extracting particles that depict a second physical property within a predetermined quantitative range; and measuring a third physical property of each extracted particle.

The first physical property may be texture, size, color, or spectral response within the zone.

The predetermined minimum heterogeneity may be a first predetermined minimum heterogeneity and identifying the zones may include identifying individual zones that depict: at least the first predetermined minimum heterogeneity of the first physical property; and at least a second predetermined minimum heterogeneity of at least one fourth physical property. The first physical property and the at least one fourth physical property may collectively include at least two of texture, size, color, and spectral response within the zone.

The second physical property may be brightness, color, contrast, hue, saturation, or wavelet energy.

The third physical property may be size or color.

Identifying the zones may include: segmenting the image based on detected boundaries between each drill cutting; and identifying the zones as those segments that individually depict at least the predetermined minimum heterogeneity of the first physical property.

Identifying the zones may include: classifying each pixel of the image based on the depicted first physical property of that pixel being within one of a plurality of predetermined value ranges of the first physical property; segmenting the image based on the pixel classifications; and identifying the zones as those segments that individually depict at least the predetermined minimum heterogeneity of the first physical property. The image segmenting may be based on neighboring ones of the pixels being classified in the same one of the predetermined value ranges.

The digital image processing may further include sorting the third physical property measurements into a plurality of predetermined value ranges. The method may further include predicting at least one geological property of the geological formation utilizing the sorted third physical property measurements. Predicting the at least one geological property may include predicting which one or more of a predetermined plurality of rock types are present in the geologic formation. Predicting the at least one geological property may further include predicting a quantity of each of the one or more rock types predicted to be present in the geologic formation. The at least one geological property may include one or more of grain size, color, and porosity of the geologic formation.

The method may further include: collecting the sample plurality of drill cuttings after retrieval from a wellbore while drilling into the geological formation to form the wellbore; and via operation of an imaging device, imaging the collected sample plurality of drill cuttings to obtain the digital image.

The method may further include: repeating the image processing on each of a plurality of additional digital images of a corresponding one of a plurality of additional samples of drill cuttings retrieved from the geological formation at corresponding subsequent times during a drilling operation; and generating a time-based log of values of the third physical property determined from the digital image and each of the additional digital images.

The method may further include: repeating the image processing on each of a plurality of additional digital images of a corresponding one of a plurality of additional samples of drill cuttings retrieved from the geological formation at different corresponding depths of a wellbore formed in the geological formation during a drilling operation; and generating a depth-based log of values of the third physical property determined from the digital image and each of the additional digital images.

The present disclosure also introduces an apparatus including a processing system having a processor and a memory storing an executable computer program code that, when executed by the processor, processes a digital image of a sample plurality of drill cuttings retrieved from a geological formation, where the digital image processing includes: identifying individual zones in the image that depict at least a predetermined minimum heterogeneity of a first physical property; in each identified zone, extracting particles that depict a second physical property within a predetermined quantitative range; and measuring a third physical property of each extracted particle.

The apparatus may further include an imaging device for obtaining the digital image.

The first physical property may be texture, size, color, or spectral response within the zone.

The second physical property may be brightness, color, contrast, hue, saturation, or wavelet energy.

The third physical property may be size or color.

One or more specific embodiments of the present disclosure are described herein. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that is within standard manufacturing or process tolerances, or which still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The Abstract at the end of this disclosure is provided to permit the reader to quickly ascertain the nature of the technical disclosure. It is submitted with the understanding that it will not be used to interpret or limit the scope or meaning of the claims.

What is claimed is:

1. A method comprising:
   processing a digital image of a sample plurality of drill cuttings retrieved from a geological formation, wherein the digital image processing comprises:
   segmenting the digital image based on detected boundaries between each drill cutting of the sample plurality of drill cuttings to generate a plurality of segments, wherein the detected boundaries follow contours of each drill cutting of the sample plurality of drill cuttings;
   classifying each segment of the plurality of segments as one classification of a plurality of classifications based on each segment depicting at least a predetermined minimum heterogeneity of a first physical property;
   identifying individual zones in the digital image, wherein each of the individual zones comprises one or more segments of the plurality of segments of a same classification of the plurality of classifications;
   in each of the individual zones, extracting particles that depict a second physical property within a predetermined quantitative range; and
   measuring a third physical property of each extracted particle.

2. The method of claim 1 wherein the first physical property is texture, size, color, or spectral response of each segment of the plurality of segments.

3. The method of claim 1 wherein:
   the predetermined minimum heterogeneity is a first predetermined minimum heterogeneity; and
   classifying each segment of the plurality of segments as one classification of the plurality of classifications based on each segment depicting:
   at least the first predetermined minimum heterogeneity of the first physical property; and
   at least a second predetermined minimum heterogeneity of at least one fourth physical property.

4. The method of claim 3 wherein the first physical property and the at least one fourth physical property collectively include at least two of texture, size, color, and spectral response of each segment of the plurality of segments.

5. The method of claim 1 wherein the second physical property is brightness, color, contrast, hue, saturation, or wavelet energy.

6. The method of claim 1 wherein the third physical property is size or color.

7. The method of claim 1 wherein the digital image processing further comprises sorting the third physical property measurements into a plurality of predetermined value ranges.

8. The method of claim 7 further comprising predicting at least one geological property of the geological formation utilizing the sorted third physical property measurements.

9. The method of claim 8 wherein predicting the at least one geological property includes predicting which one or more of a predetermined plurality of rock types are present in the geologic formation.

10. The method of claim 9 wherein predicting the at least one geological property further includes predicting a quantity of each of the one or more rock types predicted to be present in the geologic formation.

11. The method of claim 8 wherein the at least one geological property includes one or more of grain size, color, and porosity of the geologic formation.

12. The method of claim 1 further comprising:
collecting the sample plurality of drill cuttings after retrieval from a wellbore while drilling into the geological formation to form the wellbore; and
via operation of an imaging device, imaging the collected sample plurality of drill cuttings to obtain the digital image.

13. The method of claim 1 further comprising:
repeating the image processing on each of a plurality of additional digital images of a corresponding one of a plurality of additional samples of drill cuttings retrieved from the geological formation at corresponding subsequent times during a drilling operation; and
generating a time-based log of values of the third physical property determined from the digital image and each of the additional digital images.

14. The method of claim 1 further comprising:
repeating the image processing on each of a plurality of additional digital images of a corresponding one of a plurality of additional samples of drill cuttings retrieved from the geological formation at different corresponding depths of a wellbore formed in the geological formation during a drilling operation; and
generating a depth-based log of values of the third physical property determined from the digital image and each of the additional digital images.

15. An apparatus comprising:
a processing system comprising a processor and a memory storing an executable computer program code that, when executed by the processor, processes a digital image of a sample plurality of drill cuttings retrieved from a geological formation, wherein the digital image processing comprises:
segmenting the digital image based on detected boundaries between each drill cutting of the sample plurality of drill cuttings to generate a plurality of segments, wherein the detected boundaries follow contours of each drill cutting of the sample plurality of drill cuttings;
classifying each segment of the plurality of segments as one classification of a plurality of classifications based on each segment depicting at least a predetermined minimum heterogeneity of a first physical property;
identifying individual zones in the digital image, wherein each of the individual zones comprise one or more segments of the plurality of segments of a same classification of the plurality of classifications;
in each of the individual zones, extracting particles that depict a second physical property within a predetermined quantitative range; and
measuring a third physical property of each extracted particle.

16. The apparatus of claim 15 further comprising an imaging device for obtaining the digital image.

17. The apparatus of claim 15 wherein:
the first physical property is texture, size, color, or spectral response within the zone;
the second physical property is brightness, color, contrast, hue, saturation, or wavelet energy; and
the third physical property is size or color.

18. The method of claim 1 wherein the predetermined minimum heterogeneity comprises values of the first physical property that vary by at least fifty percent within each segment of the plurality of segments.

19. The method of claim 1 wherein the second physical property is different from the first physical property and the third physical property is different from the first physical property and the second physical property.

20. The apparatus of claim 15 wherein the digital image processing further comprises sorting the third physical property measurements into a plurality of predetermined value ranges.

* * * * *